US010159780B2

(12) United States Patent
Masuda

(10) Patent No.: US 10,159,780 B2
(45) Date of Patent: Dec. 25, 2018

(54) CIRCULATING SYSTEM FOR IN-BODY-CAVITY LIQUID PERFUSION AND METHOD FOR CONTROLLING SAME

(71) Applicant: NIKKISO CO., LTD., Tokyo (JP)

(72) Inventor: Yoshimichi Masuda, Higashimurayama (JP)

(73) Assignee: NIKKISO CO., LTD., Tokyo (JP)

( * ) Notice: Subject to any disclaimer, the term of this patent is extended or adjusted under 35 U.S.C. 154(b) by 174 days.

(21) Appl. No.: 15/111,017

(22) PCT Filed: Jan. 29, 2015

(86) PCT No.: PCT/JP2015/052484
§ 371 (c)(1),
(2) Date: Jul. 12, 2016

(87) PCT Pub. No.: WO2015/119032
PCT Pub. Date: Aug. 13, 2015

(65) Prior Publication Data
US 2016/0331887 A1 Nov. 17, 2016

(30) Foreign Application Priority Data

Feb. 6, 2014 (JP) .................................. 2014-021046

(51) Int. Cl.
A61M 3/02 (2006.01)
A61M 1/00 (2006.01)

(52) U.S. Cl.
CPC ........ A61M 3/0229 (2013.01); A61M 1/0058 (2013.01); A61M 3/0258 (2013.01); A61M 3/0287 (2013.01); A61M 2205/18 (2013.01); A61M 2205/3331 (2013.01); A61M 2205/3337 (2013.01); A61M 2205/3379 (2013.01);
(Continued)

(58) Field of Classification Search
CPC . A61M 1/0052; A61M 1/0056; A61M 3/0229
See application file for complete search history.

(56) References Cited

U.S. PATENT DOCUMENTS 3,900,022 A 8/1975 Widran
5,246,422 A 9/1993 Favre
5,423,738 A * 6/1995 Robinson ................ A61M 1/34
604/28

FOREIGN PATENT DOCUMENTS

JP H04507057 A 12/1992
JP 2013-135805 A 7/2013

OTHER PUBLICATIONS

Mar. 31, 2015 Search Report issued in International Patent Application No. PCT/JP2015/052484.

* cited by examiner

Primary Examiner — Nathan R Price
Assistant Examiner — Melissa A Snyder
(74) Attorney, Agent, or Firm — Oliff PLC

(57) ABSTRACT

This system for in-body-cavity liquid perfusion of a circulating type which circulates a liquid such as an isotonic solution perfused within the body cavity, suppresses an excessive increase in internal pressure that would lead to breakage of a hollow fiber membrane module. A drain valve is connected to a drain port of the hollow fiber membrane module. A pressure sensor measures the internal pressure of the hollow fiber membrane module. A control unit opens the drain valve on the basis of the internal pressure of the hollow fiber membrane module measured by the pressure sensor, draining foreign matter from the hollow fiber membrane.

6 Claims, 1 Drawing Sheet

(52) U.S. Cl.
CPC . *A61M 2205/36* (2013.01); *A61M 2205/3653* (2013.01); *A61M 2205/705* (2013.01); *A61M 2205/75* (2013.01); *A61M 2205/7545* (2013.01); *A61M 2205/7554* (2013.01); *A61M 2205/7563* (2013.01); *A61M 2210/1021* (2013.01)

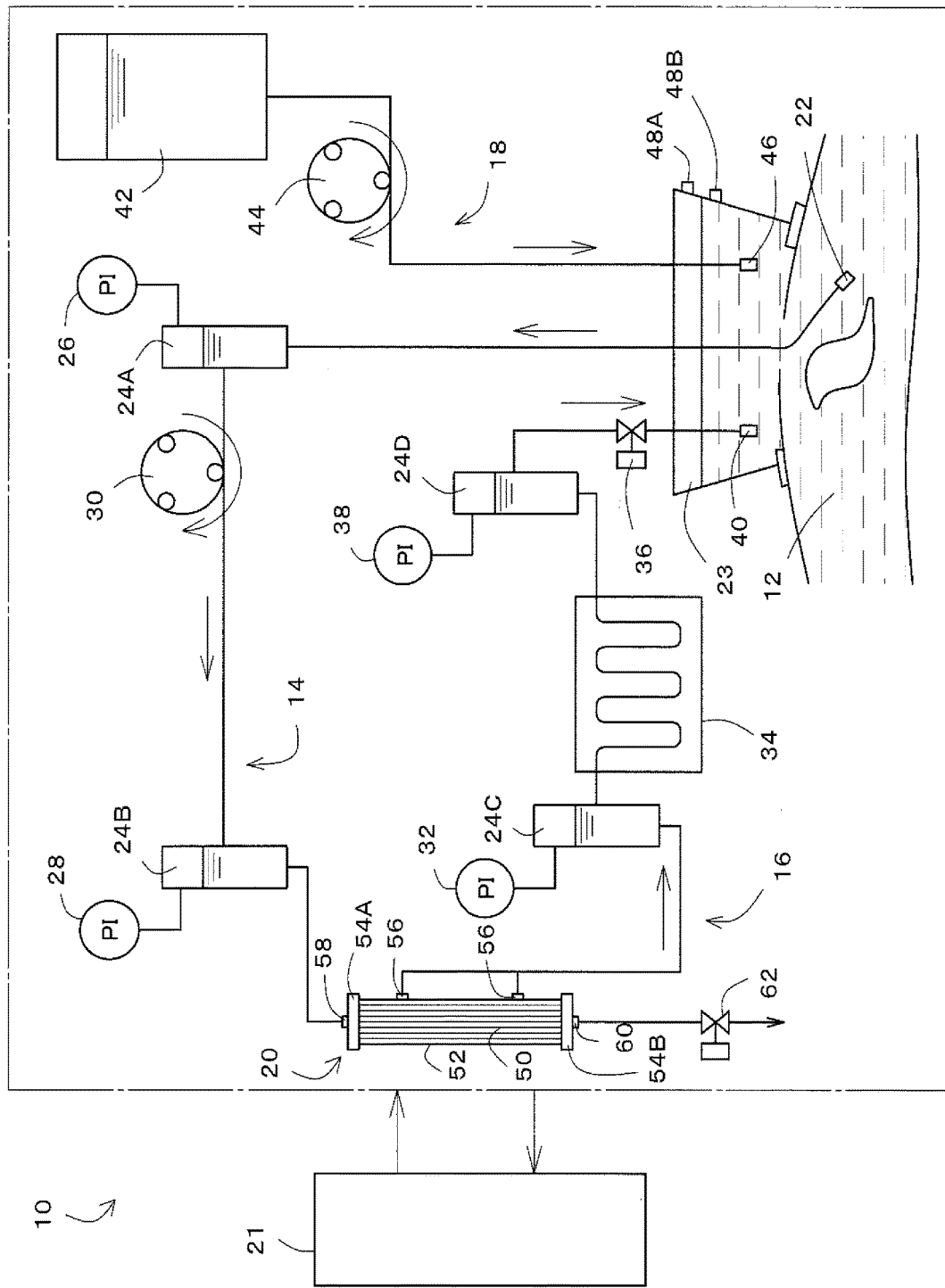

CIRCULATING SYSTEM FOR IN-BODY-CAVITY LIQUID PERFUSION AND METHOD FOR CONTROLLING SAME

TECHNICAL FIELD

The present invention relates to an in-cavity liquid perfusion system of a circulating type for circulating a liquid such as an isotonic solution perfused into a body cavity, and to a method for controlling the in-cavity liquid perfusion system of a circulating type.

BACKGROUND

In surgical operations, such as an endoscopic operation, an isotonic solution has conventionally been perfused into an abdominal cavity to secure a space in which an endoscope and surgical instruments can be placed within the abdominal cavity (refer to Patent Document 1, for example). In a case where the isotonic solution is perfused in the abdominal cavity as described above, occurrence of bleeding or the presence of a floating tissue piece during surgery performed in a body cavity will cause the isotonic solution to become cloudy, which, in turn, makes an endoscopic field blurred. For this reason, a mixture liquid of the isotonic solution and a foreign substance, such as blood, is discharged out of the body to remove the foreign substance through filtering means, and the filtered isotonic solution is reinfused (returned) into the abdominal cavity.

As the filtering means, for example, hollow fiber membrane modules are used. In such a hollow fiber membrane module, a bundle of hollow fiber membranes is housed within a cylindrically shaped column. The mixture liquid of the isotonic solution and foreign substance is made to flow from end openings of the hollow fiber membranes into the hollow fiber membranes. The mixture liquid is filtered through the hollow fiber membranes to isolate the foreign substance from the isotonic solution. The filtered isotonic solution is feed into the body cavity again.

CITATION LIST

Patent Literature

Patent Document 1: JP H04-507057 A

SUMMARY

Technical Problem

When filtration of the mixture liquid is continued over a long period in time, the foreign substance is accumulated within the hollow fiber membranes, and an internal pressure of the hollow fiber membrane module is accordingly increased. This condition poses a risk of damage to the hollow fiber membrane module.

Solution to Problem

The present invention relates to an in-cavity liquid perfusion system of a circulating type for isolating a foreign substance from a mixture liquid of an isotonic solution and the foreign substance extracted from a body cavity and returning the isotonic solution into the body cavity. This system has a hollow fiber membrane module that houses a bundle of hollow fiber membranes and includes an inflow port from which the mixture liquid is introduced through one open end of the bundle of hollow fiber membranes into the hollow fiber membranes, a liquid return port from which the isotonic solution filtered through the bundle of hollow fiber membranes and isolated from the foreign substance is returned, and a discharge port connected to the other open end of the bundle of the hollow fiber membranes. The system further includes a discharge valve connected to the discharge port, a pressure sensor that measures an internal pressure of the hollow fiber membrane module, and a control unit configured to cause, based on the internal pressure of the hollow fiber membrane module, the discharge valve to be opened, to thereby discharge the foreign substance from the hollow fiber membranes.

Further, in the above invention, it is preferable that the system further includes a replenisher solution pump that delivers the isotonic solution from a replenisher solution container to the body cavity, and the control unit is configured to feed the isotonic solution into the body cavity through the replenisher solution pump so as to compensate for a portion of the mixture liquid discharged out by opening the discharge valve.

Still further, in the above-described invention, it is preferable that the system further includes a circulation pump that directs the mixture liquid to the inflow port, and the control unit is configured to cause the circulation pump and the replenisher solution pump to be driven in synchronism with each other during a period in which the discharge valve is open.

Moreover, in the above-described invention, it is preferable that a liquid return channel from the liquid return port to the body cavity is equipped with a liquid return valve for controlling a flow rate of the isotonic solution that is returned into the body cavity, and the control unit is configured to cause the liquid return valve to be closed during a period in which the circulation pump and the replenisher solution pump are driven in synchronism with each other.

Further, in the above-described invention, it is also preferable that the system includes a liquid vessel that is placed on a body wall to store the isotonic solution, the liquid vessel is equipped with a level sensor that detects a liquid level of the isotonic solution, and the control unit is configured to cause the replenisher solution pump to be actuated depending on the liquid level.

The present invention also relates to a control method for an in-cavity liquid perfusion system of a circulating type for isolating a foreign substance from a mixture liquid of an isotonic solution and the foreign substance extracted from a body cavity and returning the isotonic solution into the body cavity. The control method includes delivering the mixture liquid from an inflow port into a hollow fiber membrane module, which houses a bundle of hollow fiber membranes and includes the inflow port from which the mixture liquid is introduced through one open end of the bundle of hollow fiber membranes into the hollow fiber membranes, a liquid return port from which the isotonic solution filtered through the bundle of hollow fiber membranes and isolated from the foreign substance is returned, and a discharge port connected to the other open end of the bundle of hollow fiber membranes, measuring an internal pressure of the hollow fiber membrane module into which the mixed liquid is delivered, and causing the discharge valve connected to the discharge port to be opened based on the measured internal pressure of the hollow fiber membrane module for discharging the foreign substance out of the hollow fiber membranes.

Advantageous Effects of Invention

According to the present invention, an excessive increase in internal pressure that will result in damage to the hollow fiber membrane module can be prevented.

BRIEF DESCRIPTION OF DRAWINGS

FIG. 1 is a diagram illustrating an in-cavity liquid perfusion system according to an embodiment of this invention.

DESCRIPTION OF EMBODIMENTS

FIG. 1 shows, by way of example, an in-cavity liquid perfusion system 10 according to an embodiment of this invention. The in-cavity liquid perfusion system 10, which is of a so-called circulating type, extracts a mixture liquid of an isotonic solution and a foreign substance from the inside of a body cavity 12, isolates (filters out) the foreign substance from the mixture liquid, and returns the filtered isotonic solution into the body cavity 12. It should be noted that endoscope equipment and surgical instruments are not illustrated in FIG. 1.

The in-cavity liquid perfusion system 10 includes a mixture liquid channel 14, a liquid return channel 16, a replenisher solution channel 18, a hollow fiber membrane module 20, a control unit 21, and a liquid vessel 23.

The mixture liquid channel 14 is a flow channel for directing the mixture liquid of the isotonic solution and the foreign substance, such as blood or a tissue piece, from the body cavity 12 into the hollow fiber membrane module 20. The mixture liquid channel 14 is equipped with a suction port 22, air trap chambers 24A and 24B, a suction side pressure sensor 26, an inflow side pressure sensor 28, and a circulation pump 30.

The suction port 22 is a sucking port member placed within the body cavity 12 to suck out the mixture liquid of the isotonic solution and the foreign substance. The air trap chamber 24A is arranged, for example, between the suction port 22 and the circulation pump 30. The air trap chamber 24A is a gas-liquid separator for removing air from the mixture liquid. Further, the air trap chamber 24A is a sealed structure, in which an internal pressure of the air trap chamber 24A is changed depending on a volume of the mixture liquid that is caused to flow into the air trap chamber 24A. An empty space is provided above a liquid level in the air trap chamber 24A.

The suction side pressure sensor 26 measures a liquid pressure of the sucked mixture liquid. More specifically, the internal pressure of the air trap chamber 24A is measured, to thereby find a liquid pressure of the sucked mixture liquid. The suction side pressure sensor 26 is joined to the space provided above the liquid level in the air trap chamber 24A. This can prevent physical contact between the suction side pressure sensor 26 and the mixture liquid.

The circulation pump 30 causes the mixture liquid to flow from the inside of the body cavity 12 through an inflow port 58 into the hollow fiber membrane module 20. Preferably, the circulation pump 30 is of a contactless type that does not make contact with the mixture liquid. For example, the circulation pump 30 may be composed of a roller pump. In particular, the roller pump is arranged to contact the outside of a flexible tube through which the mixture liquid is transported, and is configured to squeeze the flexible tube from a body cavity 12 side toward the hollow fiber membrane module 20. In this way, the mixture liquid within the flexible tube is introduced into the hollow fiber membrane module 20.

The air trap chamber 24B may be arranged between the circulation pump 30 and the hollow fiber membrane module 20. The inflow side pressure sensor 28 is a pressure sensor for measuring a pressure of the mixture liquid to be flown into the hollow fiber membrane module 20. The inflow side pressure sensor 28 is joined to the space above the level of the mixture liquid inside the air trap chamber 24B in the same manner as that of the suction side pressure sensor 26.

The liquid return channel 16 is a flow channel through which the isotonic solution isolated from the foreign substance (filtered) through the hollow fiber membrane module 20 is returned into the body cavity 12. The liquid return channel 16 is equipped with air trap chambers 24C and 24D, an outflow side pressure sensor 32, a warmer 34, a liquid return valve 36, a liquid return side pressure sensor 38, and a liquid return port 40.

The outflow side pressure sensor 32 measures a liquid pressure of the isotonic solution that is caused to flow out from the hollow fiber membrane module 20. The outflow side pressure sensor 32 measures the liquid pressure via the air trap chamber 24C in a contactless manner similar to that of the suction side pressure sensor 26 and the inflow side pressure sensor 28.

When a discharge valve 62, which will be described below, is closed, a difference between a pressure value measured by the inflow side pressure sensor 28 and a pressure value measured by the outflow side pressure sensor 32 is considered to indicate the internal pressure of the hollow fiber membrane module 20 (the pressure received by the hollow fiber membranes from the mixture liquid flown therein). For this reason, both the inflow side pressure sensor 28 and the outflow side pressure sensor 32 function as a pressure sensor for measuring the internal pressure of the hollow fiber membrane module 20.

The warmer 34 warms the isotonic solution to be returned into the body cavity 12 to an approximate body temperature. The warmer 34 is composed of, for example, a plate heater.

The air trap chamber 24D separates the isotonic solution to be delivered to the body cavity 12 into gas and liquid. The liquid return side pressure sensor 38 measures via the air trap chamber 24D a liquid pressure of the isotonic solution to be returned into the body cavity 12 without contacting the isotonic solution.

The liquid return valve 36 is provided somewhere between the liquid return port 56 and the body cavity 12 to control the flow rate of the isotonic solution. For example, the liquid return valve 36 is arranged between the air trap chamber 24D and the liquid return port 40.

The replenisher solution channel 18 supplies the body cavity 12 with the isotonic solution, as will be described below, to compensate for a discharged portion of the mixture liquid that is discharged from the hollow fiber membrane module 20. The replenisher solution channel 18 is equipped with a replenisher solution container 42, a replenisher solution pump 44, and a replenisher solution port 46.

The replenisher solution container 42 stores the same isotonic solution as the isotonic solution being supplied to the body cavity 12. The replenisher solution pump 44 is arranged between the replenisher solution container 42 and the replenisher solution port 46, to introduce the isotonic solution from the replenisher solution container 42 into the body cavity 12. The replenisher solution pump 44 may be a roller pump, and the roller pump is preferably the same as the circulation pump 30 with respect to a liquid feeding amount per unit number of revolutions.

The liquid vessel 23 is placed on the body wall in a position surrounding an incision in the body cavity 12. The liquid vessel 23 may be formed substantially in the shape of, for example, a frustum of a circular cone, and is open on its top. The bottom surface of the liquid vessel 23 has a through hole, and the liquid vessel 23 is placed on the body wall in such a manner that the through hole is aligned with the incision. In the liquid vessel 23, the isotonic solution is stored. The stored isotonic solution is made to flow from the through hole into the body cavity 12.

The liquid vessel 23 is equipped with level sensors 48A and 48B for measuring a liquid level. The level sensors 48A and 48B are level sensors of a contactless type, such as, for example, an optical type or an ultrasonic type, and are attached to a side wall of the liquid vessel 23. Alternatively, a level sensor of a contact type, such as a float type, may be used in place of the contactless level sensors.

The hollow fiber membrane module 20 is a filtering member for separating the mixture liquid of the isotonic solution and foreign substance into the isotonic solution and the foreign substance. The hollow fiber membrane module 20 includes a hollow fiber membrane bundle 50, a housing 52, and liquid passage caps 54A and 54B.

The hollow fiber membrane bundle 50 is a bundle of hollow fibers which are open at both ends along the longitudinal direction. The housing 52 is a cylindrically shaped member in which the hollow fiber membrane bundle 50 is housed. Non-illustrated sealing members are fixedly attached to an inner circumferential surface of the housing 52 at the both ends thereof, to fix the hollow fiber membrane bundle 50 onto the housing 52. In addition, the inside of the housing 52 is partitioned into two regions inside the hollow fiber membranes and outside the hollow fiber membranes. Further, the housing 52 is equipped with liquid return ports 56 that are connected to the liquid return channel 16, and the liquid return ports 56 are arranged to communicate with the region outside the hollow fiber membranes. It should be noted that although the two liquid return ports 56 are illustrated in the drawing, a single liquid return port or more than two liquid return ports may be provided.

The liquid passage caps 54A and 54B are lid members which are attached to both end portions of the housing 52, respectively. The inflow port 58 is disposed on the liquid passage cap 54A, while the discharge port 60 is disposed on the liquid passage cap 54B. The discharge port 60 communicates with the region inside the hollow fiber membranes.

The inflow port 58 is connected to a distal end of the mixture liquid channel, and configured to deliver the mixture liquid from one of open ends of the hollow fiber membrane bundle 50 into the hollow fiber membranes. The discharge port 60 is able to discharge foreign substances that are accumulated within the hollow fiber membranes, as will be described below. The discharge valve 62 is connected to a point located downstream of the discharge port 60.

The control unit 21 controls each of the devices arranged on a perfusion path to adjust circulation of the isotonic solution. The control unit 21 is able to receive signals from the devices and perform calculation on the received signals, and is also able to generate and send control signals to the devices. The control unit 21 may be, for example, a computer in which a calculation circuit and a storage unit are installed.

The control unit 21 receives a measurement value of the liquid pressure from each of the pressure sensors including the suction side pressure sensor 26, the inflow side pressure sensor 28, the outflow side pressure sensor 32, and the liquid return side pressure sensor 38. Further, the control unit 21 receives the liquid level in the liquid vessel 23 from the level sensors 48A and 48B. Still further, the control unit 21 operates, based on the received measurement values, the circulation pump 30, the replenisher solution pump 44, the liquid return valve 36, and the discharge valve 62.

Circulation control performed by the control unit 21 will be described below. As an initial state of circulation of the isotonic solution, the control unit 21 closes the discharge valve 62, and opens the liquid return valve 36. Then, in addition to causing the replenisher solution pump 44 to stop, the control unit 21 controls actuation of the circulation pump 30 in such a manner that the mixture liquid is made to flow at a predetermined flow rate through the mixture liquid channel 14. The mixture liquid is successively supplied to the hollow fiber membrane module 20 where the mixture liquid is filtered through the hollow fiber membrane bundle to isolate the foreign substance from the mixture liquid. After the isolation, the isotonic solution is returned from the liquid return ports 56 through the liquid return channel 16 into the body cavity 12.

The control unit 21 calculates, from a difference between the measurement values of the inflow side pressure sensor 28 and the outflow side pressure sensor 32, an internal pressure of the hollow fiber membrane module 20. As a greater amount of the foreign substance is accumulated within the hollow fiber membranes, the internal pressure of the hollow fiber membrane module 20 is increased. The control unit 21 causes the discharge valve 62 to be opened when the internal pressure of the hollow fiber membrane module 20 is increased to a predetermined value. This allows the foreign substances accumulated in the hollow fiber membranes to be discharged out of the hollow fiber membrane module 20.

A value of the internal pressure of the hollow fiber membrane module at which the discharge valve 62 is opened is determined based on a maximum withstand pressure value of the hollow fiber membrane module 20. For example, when the value of the internal pressure reaches 70% of the maximum withstand pressure value of the hollow fiber membrane module 20, the discharge valve 62 is opened.

The opening of the discharge valve 62 allows the mixture liquid flowing through the hollow fiber membrane bundle 50 to wash out the foreign matter accumulated within the hollow fiber membranes. More specifically, the foreign matter is delivered while being entrained in the mixture liquid that is discharged out of a circulation system. Then, to compensate for a discharged portion of the mixture liquid, the control unit 21 actuates the replenisher solution pump 44 to feed the isotonic solution into the body cavity 12.

During a period in which the discharge valve 62 is open, the control unit 21 causes the circulation pump 30 and the replenisher solution pump 44 to be driven in synchronism with each other. Here, being driven in synchronism particularly means that a feeding amount of the mixture liquid by means of the circulation pump 30 is equated with a feeding amount of the isotonic solution by means of the replenisher solution pump 44. In this way, it becomes possible to feed, through the replenisher solution pump 44, the isotonic solution which is of the same volume as that of the mixture liquid discharged from the discharge valve 62.

Even in the period in which the discharge valve 62 is open, a portion of the mixture liquid inside the hollow fiber membrane module 20 may sometimes be filtered through the hollow fiber membranes and made to flow into the liquid return channel 16. If this is the case, a discharge rate of the hollow fiber membrane module 20 will become lower than the flow rate of the mixture liquid delivered by the circulation pump 30. In this state, the synchronized driving of the circulation pump 30 and the replenisher solution pump 44 results in an excessive amount of the isotonic solution being supplied, which poses a risk of an overflow of the isotonic solution from the liquid vessel 23. With this in mind, the control unit 21 may cause the liquid return valve 36 to be closed for halting the returning of the isotonic solution into the body cavity 12 during the period of the synchronized driving of the circulation pump 30 and the replenisher solution pump 44.

Meanwhile, the control unit 21 determines from the measurement values of the level sensors 48A and 48B whether or not the liquid level in the liquid vessel 23 falls within a predetermined allowable range, and checks, based on the result of determination, operating conditions of the circulation pump 30 and the replenisher solution pump 44. For example, when the liquid level in the liquid vessel 23 falls below the predetermined allowable range, the flow rate of the isotonic solution by means of the replenisher solution pump 44 is increased. On the other hand, when the liquid level in the liquid vessel 23 exceeds the allowable range, for example, the flow rate of the isotonic solution by means of the replenisher solution pump 44 is reduced, or the replenisher solution pump 44 is stopped. In addition to this, the isotonic solution that has exceeded the liquid level in the liquid vessel 23 may be drained out from the discharge valve 62 by the circulation pump 30. In this way, the liquid level can be lowered to a value within the allowable range.

Stabilization of the liquid level within the liquid vessel 23 can provide an effect of, when a surgical operation is performed on an organ, such as an intestinal tract, which is drawn into the liquid vessel 23, protecting the surface of the organ from drying or being damaged (adhered). Meanwhile, minor bleeding from a surgical wound can be stopped by the liquid pressure. The stabilization of the liquid level inside the liquid vessel 23 can further provide an effect that the body cavity is fully filled with the isotonic solution. This means that the air, which acts as a source of noise in ultrasonic echo diagnosis or the like, can be prevented from entering the abdominal cavity.

In addition, deterioration in hygienic conditions (development of infection) or other adverse influence can be avoided in a surgical environment by preventing the overflow of the isotonic solution (the mixture liquid) from the liquid vessel 23. Further, a situation in which a portion of the mixture liquid is unrecovered due to the overflow can be avoided from occurring.

As described above, in the in-cavity liquid perfusion system 10 of a circulating type according to this embodiment, the mixture liquid discharged from the discharge valve 62 can be compensated for by the replenisher of the isotonic solution, to thereby maintain the feed rate of the isotonic solution into the body cavity 12. In addition, even in the absence of the fluid meter, such as a flowmeter, attached to the discharge valve 62, the feed rate of the isotonic solution can be managed by synchronously driving the circulation pump 30 and the replenisher solution pump 44, and supplying the isotonic solution based on the liquid level in the liquid vessel 23. It is necessary for the fluid meter to be replaced on a regular basis in light of the situation that the fluid meter makes contact with the mixture liquid, which is a contributing factor to increased running costs. According to the present embodiment, however, the necessity to attach the fluid meter can be eliminated, which can, in turn, lead to a decrease in cost.

The control unit 21 continuously monitors the measurement value of the inflow side pressure sensor 28, and causes the discharge valve 62 to be closed when the measurement value is decreased to a predetermined value. Further, the control unit 21 stops the replenisher solution pump 44, and causes the liquid return valve 36 to be opened. A value of pressure for causing the discharge valve 62 to be closed may be an atmospheric pressure, for example.

There may be cases where even after the discharge valve 62 is opened, the pressure value of the inflow side pressure sensor 28 keeps increasing due to a failure of the discharge valve 62, kinking (bending) of the flexible tube within the flow channel, or other faults. In such a case, the control unit 21 may deactivate the circulation pump 30 and the replenisher solution pump 44 in addition to performing processing in response to an abnormal condition, such as an issuance of an abnormality alarm.

It should be noted that although the liquid return valve 36 is inserted into the liquid return channel 16 in the above-described embodiment, the embodiment is not limited to this form. For example, the liquid return valve 36 may be omitted, and the replenisher solution pump 44 may be actuated based on the liquid level from the level sensors 48A and 48B.

In addition, the difference between the pressure value of the inflow side pressure sensor 28 and the pressure value of the outflow side pressure sensor 32 is obtained in order to find the internal pressure of the hollow fiber membrane module 20. However, the embodiment is not limited to this form. For example, when a value of the liquid pressure inside the liquid return channel is approximately equal to the atmospheric pressure, the pressure value from the inflow side pressure sensor 28 may be used as the value of the internal pressure of the hollow fiber membrane module 20.

Moreover, a roller pump may be provided in place of the discharge valve 62. Specifically, when the internal pressure of the hollow fiber membrane module 20 is increased to a predetermined value, the roller pump is actuated, to discharge the foreign substance out of the hollow fiber membranes. As long as the number of revolutions (rotational speed) of the roller pump and the diameter of a tube squeezed by the roller pump are known, a discharge rate achieved by action of the roller pump can be calculated from the number of revolutions and the diameter of the tube. Because of this, the amount of the isotonic solution to be replenished can be found with a higher degree of accuracy although the use of the roller pump results in a higher cost compared with a case of using the discharge valve 62.

REFERENCE SIGN LIST 10 in-cavity liquid perfusion system; 12 body cavity; 14 mixture liquid channel; 16 liquid return channel; 18 replenisher solution channel; 20 hollow fiber membrane module; 21 control unit; 23 liquid vessel; 28 inflow side pressure sensor; 30 circulation pump; 32 outflow side pressure sensor; 36 liquid return valve; 42 replenisher solution container; 44 replenisher solution pump; 48A, 48B level sensor; 50 hollow fiber membrane bundle; 56 liquid return port; 58 inflow port; 60 discharge port; 62 discharge valve.

The invention claimed is:

1. An in-cavity liquid perfusion system of a circulating type for isolating a foreign substance from a mixture liquid of an isotonic solution and the foreign substance extracted from a body cavity and returning the isotonic solution into the body cavity, the in-cavity liquid perfusion system comprising:

a hollow fiber membrane module which houses a bundle of hollow fiber membranes and comprises an inflow port from which the mixture liquid is delivered from one open end of the bundle of hollow fiber membranes into the hollow fiber membranes, a liquid return port from which the isotonic solution filtered through the bundle of hollow fiber membranes and separated from the foreign substance is returned, and a discharge port connected to the other open end of the bundle of hollow fiber membranes;

a discharge valve connected to the discharge port;

a pressure sensor that measures an internal pressure of the hollow fiber membrane module; and a control unit configured to cause the discharge valve to be opened based on the internal pressure of the hollow fiber membrane module, to discharge the foreign substance out of the hollow fiber membranes.

2. The in-cavity liquid perfusion system of a circulating type according to claim 1, further comprising:

a replenisher solution pump configured to direct the isotonic solution from a replenisher solution container into the body cavity, wherein the control unit is configured to feed the isotonic solution into the body cavity through the replenisher solution pump to compensate for a portion of the mixture liquid discharged out by opening the discharge valve.

3. The in-cavity liquid perfusion system of a circulating type according to claim 2, further comprising:

a circulation pump configured to deliver the mixture liquid to the inflow port, wherein the control unit is configured to cause the circulation pump and the replenisher solution pump to be driven in synchronism with each other during a period in which the discharge valve is open.

4. The in-cavity liquid perfusion system of a circulating type according to claim 3, wherein:

a liquid return channel from the liquid return port to the body cavity is equipped with a liquid return valve configured to control a flow rate of the isotonic solution to be returned into the body cavity; and the control unit is configured to cause the liquid return valve to be closed during a period in which the circulation pump and the replenisher solution pump are driven in synchronism with each other.

5. The in-cavity liquid perfusion system of a circulating type according to claim 2, further comprising:

a liquid vessel configured to be placed on a body wall and configured to store the isotonic solution, wherein a level sensor is configured to measure a liquid level of the isotonic solution is attached to the liquid vessel, and the control unit is configured to actuate the replenisher solution pump depending on the liquid level.

6. A method for controlling an in-cavity liquid perfusion system of a circulating type for isolating a foreign substance from a mixture liquid of an isotonic solution and the foreign substance extracted from a body cavity and returning the isotonic solution into the body cavity, the method comprising:

delivering the mixture liquid from an inflow port to a hollow fiber membrane module which houses a bundle of hollow fiber membranes and comprises the inflow port from which the mixture liquid is delivered from one open end of the bundle of hollow fiber membranes into the hollow fiber membranes, a liquid return port from which the isotonic solution filtered through the bundle of hollow fiber membranes and isolated from the foreign substance is returned; and a discharge port connected to the other open end of the bundle of hollow fiber membranes;

measuring an internal pressure of the hollow fiber membrane module into which the mixture liquid has been delivered;

opening a discharge valve connected to the discharge port based on the measured internal pressure of the hollow fiber membrane module to discharge the foreign substance out of the hollow fiber membranes.

* * * * *